(12) United States Patent
Sato et al.

(10) Patent No.: US 12,262,907 B2
(45) Date of Patent: Apr. 1, 2025

(54) ORGAN SUCKING AND GRASPING TOOL

(71) Applicants: KYOTO UNIVERSITY, Kyoto (JP); FUJI SYSTEMS CORPORATION, Tokyo (JP)

(72) Inventors: Toshihiko Sato, Kyoto (JP); Yusuke Muranishi, Kyoto (JP); Akihiro Asai, Kanagawa (JP)

(73) Assignees: KYOTO UNIVERSITY, Kyoto (JP); FUJI SYSTEMS CORPORATION, Tokyo (JP)

( * ) Notice: Subject to any disclaimer, the term of this patent is extended or adjusted under 35 U.S.C. 154(b) by 770 days.

(21) Appl. No.: 17/611,254

(22) PCT Filed: Apr. 23, 2020

(86) PCT No.: PCT/JP2020/017484
§ 371 (c)(1),
(2) Date: Nov. 15, 2021

(87) PCT Pub. No.: WO2020/230575
PCT Pub. Date: Nov. 19, 2020

(65) Prior Publication Data
US 2022/0226011 A1    Jul. 21, 2022

(30) Foreign Application Priority Data
May 16, 2019   (JP) .................................. 2019-092810

(51) Int. Cl.
*B25J 15/06*     (2006.01)
*A61B 17/30*    (2006.01)

(52) U.S. Cl.
CPC ........... *A61B 17/30* (2013.01); *B25J 15/0683* (2013.01); *A61B 2017/306* (2013.01)

(58) Field of Classification Search
CPC ......... A61B 2017/306; A61B 2017/308; B25J 15/0683; B25J 15/06
See application file for complete search history.

(56) References Cited

U.S. PATENT DOCUMENTS 6,641,604 B1 * 11/2003 Adelman ............... A61B 17/02
600/37
6,663,622 B1 * 12/2003 Foley ................. A61B 18/1492
606/41

(Continued)

FOREIGN PATENT DOCUMENTS

| CN | 101991441 A | 3/2011 |
| EP | 2283778 A2 | 2/2011 |

(Continued)

OTHER PUBLICATIONS

Office Action issued in corresponding Chinese Patent Application No. 202080024693.1 dated Apr. 19, 2024.

(Continued)

*Primary Examiner* — Douglas A Hess
(74) *Attorney, Agent, or Firm* — TROUTMAN PEPPER LOCKE LLP (57) ABSTRACT

Disclosed is an organ sucking and grasping tool capable of reducing the height of the sucking and grasping tool, capable of reserving a viewing field for an endoscope, capable of reserving space for operations, and including a suction cup responsive to the deformation of an organ and unlikely to be detached. An organ sucking and grasping tool includes a suction tube body and a plurality of suction cups for organ suction provided at a front end portion of the suction tube body. The organ sucking and grasping tool sucks, elevates, and grasps an organ using suction force generated by the suction cups. The suction cups are held by a ring-shaped holder provided at the front end portion of the tube body, and (Continued)

an annular flange is provided at an open end portion of each of the suction cups.

5 Claims, 9 Drawing Sheets

(56) References Cited

U.S. PATENT DOCUMENTS

| | | | | |
|---|---|---|---|---|
| 6,852,075 | B1* | 2/2005 | Taylor | A61B 17/0218 600/37 |
| 7,097,612 | B2* | 8/2006 | Bertolero | A61B 17/0206 600/231 |
| 7,479,104 | B2* | 1/2009 | Lau | A61M 1/80 600/37 |
| 2003/0139646 | A1 | 7/2003 | Sharrow et al. | |
| 2009/0030270 | A1 | 1/2009 | Arai et al. | |
| 2009/0326518 | A1* | 12/2009 | Rabin | A61B 17/0218 606/1 |

FOREIGN PATENT DOCUMENTS

| | | |
|---|---|---|
| JP | 2003-529403 A | 10/2003 |
| JP | 2005-515014 A | 5/2005 |
| JP | 4406716 B2 | 11/2009 |
| JP | 4556949 B2 | 7/2010 |
| JP | 2017-202093 A | 11/2017 |
| WO | 01/17437 A2 | 3/2001 |
| WO | 02/054937 A2 | 7/2002 |

OTHER PUBLICATIONS

International Search Report issued in International Patent Application No. PCT/JP2020/017484 dated Jul. 14, 2020, with English translation.

* cited by examiner

ORGAN SUCKING AND GRASPING TOOL

CROSS REFERENCE TO RELATED APPLICATIONS

The present application is a U.S. National Phase Application under 35 U.S.C. § 371 of International Patent Application No. PCT/JP2020/017484 filed Apr. 23, 2020, which claims priority to Japanese Patent Application No. 2019-092810 filed May 16, 2019. The entire contents of which are hereby incorporated by reference.

TECHNICAL FIELD

The present invention relates to an organ sucking and grasping tool, more specifically, to a technique for facilitating a surgical operation using an endoscope, for example, by elevating and grasping an organ such as a lung through suction of a surface of the organ during implementation of the operation.

BACKGROUND

During implementation of a surgical operation, for facilitating treatment on an affected part, an organ to block a viewing field is indispensably required to be handled by being elevated or excluded, for example. During implementation of an open-chest or abdominal operation, the organ is elevated with a hand of an operator or with a tool such as a surgical stabilizer. On the other hand, during implementation of a surgical operation using an endoscope that is a minimally invasive operation, a trocar is retained at a small incisional wound and a surgical instrument is inserted through the trocar. This prohibits insertion of a large instrument into a body cavity, so that the organ is elevated using forceps, for example.

The applicant suggested Japanese Laid-open Patent Publication No. 2017-202093 previously. However, actually using an organ sucking and grasping tool suggested in Japanese Laid-open Patent Publication No. 2017-202093 has found that, as a result of the presence of a dome-shaped member of the tool, the height (the length in an axis direction) of the tool becomes excessive in limited space (chest cavity) to cause a problem of bad usage during handling, treatment, etc.

Further, as a result of a configuration in which the dome-shape member covers a plurality of suction cups from behind, a viewing field for the endoscope is blocked to cause a problem of reducing space for implementation of an operation.

Another problem is also caused in that, as a result of the softness and easily-deformable property of a lung, the suction cups fail to follow and respond to change in the lung occurring by sucking and then retaining the lung (particularly, traction in a lateral direction). This causes clearances in the suction cups, thereby causing detachment and slipping off of the suction cups.

SUMMARY OF INVENTION

Thus, the present invention is intended to solve the conventional problem described above and to provide an organ sucking and grasping tool capable of reducing the height of the sucking and grasping tool, capable of reserving a viewing field for an endoscope, capable of reserving space for operations, and including a suction cup responsive to the deformation of an organ and unlikely to be detached.

To solve the foregoing problem, the invention described in one example is an organ sucking and grasping tool including a suction tube body and a plurality of suction cups for organ suction provided at a front end portion of the suction tube body. The organ sucking and grasping tool sucks, elevates, and grasps an organ using suction force generated by the suction cups. The suction cups are held by a ring-shaped holder provided at the front end portion of the tube body, and an annular flange is provided at an open end portion of each of the suction cups.

Another example is such that the holder is made of silicone rubber or soft resin, the holder includes a center boss, a plurality of suction cup attachments jutting out in a radial direction from the center boss, and a ring fixed in such a manner as to connect respective tip portions of the suction cup attachments, and a metallic wire is buried in the ring. The holder is configured to hold an end portion of each of the suction cups opposite the open end portion thereof at an attachment hole provided at the suction cup attachment.

The flange is inwardly bent from an end edge of each of the suction cups. The front end portion of the suction tube body is covered with a protective pipe and is connected to the center boss of the holder.

A coating tube is fitted to the protective pipe and has an outer peripheral surface provided with an undulated part.

The suction cups include three suction cups arranged at the holder in such a manner that a line connecting the respective centers of the suction cups form a regular triangle. The suction cups have center axes parallel to the center axis of the tube body.

With the configuration of the present invention described above, the suction cups are held by the ring-shaped holder provided at the front end portion of the tube body in the organ sucking and grasping tool. This is certainly expected to achieve working effect achieved by the conventional dome-shaped member. Further, the configuration of holding the suction cups using the ring-shape holder instead of the dome-shaped member allows reduction in the height of the organ sucking and grasping tool, thereby improving usage during handling, treatment, etc. Additionally, reservation of a viewing field for an endoscope and reservation of space for operations are facilitated, compared to the dome-shaped member. Further, the provision of the annular flange at the open end portion of the suction cup suppresses deformation even of a soft lung (organ), while making the suction cup unlikely to be detached to prevent slipping off of the suction cup.

According to the invention, the shape of the holder is retained by the metallic wire buried in the ring of the holder made of silicone rubber or soft resin so retention of the suction cup is facilitated. A provision of the inwardly bent flange eliminates a clearance at the open end portion of the suction cup to be caused by the deformation of an organ, thereby preventing the deformation of the organ more efficiently.

According to the invention, connection between the tube body and the holder is facilitated and holding with forceps can be done reliably. According to the invention, well-balanced arrangement of the three suction cups is allowed to encourage application of uniform suction force. The suction cup and the holder can be attached to the tube body while being point to the same direction. This encourages increased efficiency in the attachment to improve workability of production.

DETAILED DESCRIPTION

An organ sucking and grasping tool according to an embodiment will be described below by referring to the drawings.

Figure 5:
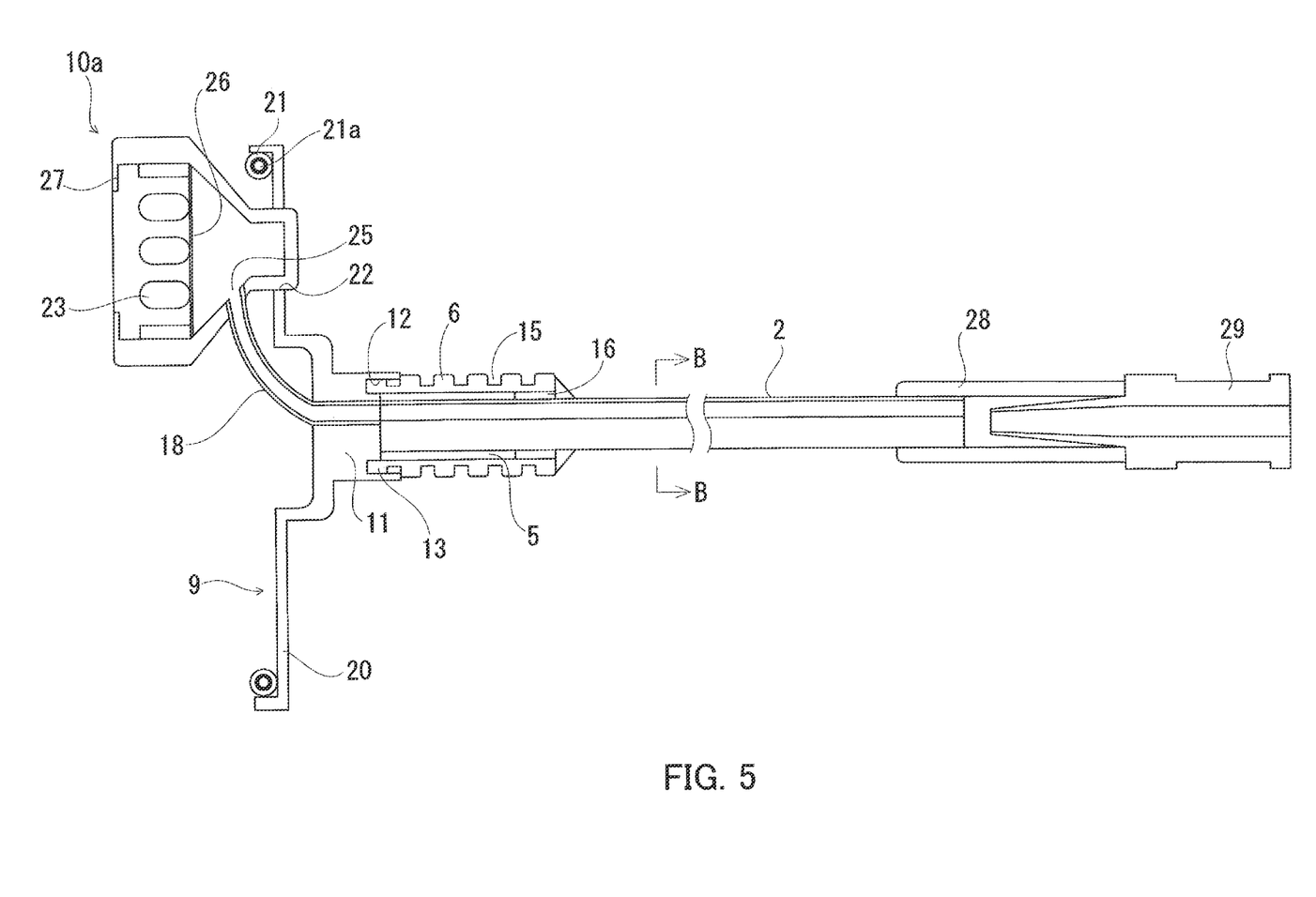
FIG. 5 is a partially-omitted enlarged cross-sectional view taken along a line A-A in FIG. 4.
Figure 6:
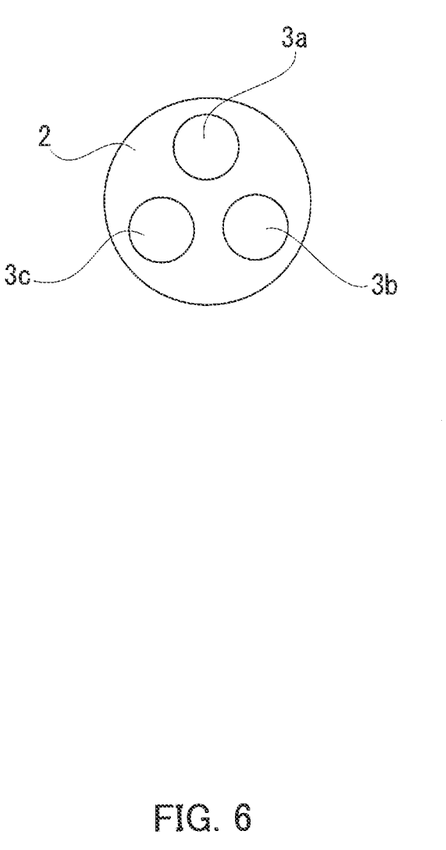
FIG. 6 is an enlarged cross-sectional view taken along a line B-B in FIG. 5.

Referring to FIGS. 1 to 6, 1 shows a sucking and grasping tool for an organ such as a lung. The sucking and grasping tool 1 includes a suction tube body 2. The tube body 2 is a three-lumen type tube with three suction lumens 3a, 3b, and 3c extending in an axis direction (FIG. 6). The tube body 2 has a front end portion to which a metallic protective pipe is fitted. A coating tube 6 is further fitted to the protective pipe 5. The front end portion of the tube body 2 where the protective pipe 5 and the coating tube 6 are fitted to be integrated with each other is fixedly coupled to a center boss 11 of a holder 9 made of silicone rubber or soft resin through an insertion fit between a recess 12 at a rear end portion of the boss and a protrusion 13 at a front end portion of the coating tube. The coating tube 6 has an outer peripheral surface provided with a plurality of annular recesses 15 arranged in an axis direction to form an undulated part. Further, 16 is a filler.

The metallic protective pipe 5 of this example is made of stainless steel. The provision of this protective pipe made of stainless steel is intended to prevent crush of the tube body 2 occurring when a corresponding part is held with forceps during implementation of an operation. Formation of the undulated part through the provision of the annular recesses 15 at the outer peripheral surface of the coating tube 6 is intended to prevent slippage occurring when a corresponding part is held with forceps.

In the present embodiment, the outer peripheral surface of the tube body 2 is not provided with a guide pipe made of a metallic pipe such as the one provided in the previously filed application (Japanese Laid-open Patent Publication No. 2017-202093). Such a guide pipe may be provided as needed, if a kink is likely to occur during use, for example. This reduces the occurrence of a kink to allow traction of a large organ. If the guide pipe is provided, the outer peripheral surface of the guide pipe may be covered with an additional coating tube to prevent damage on a body tissue during use.

The center boss 11 functions as a core of the holder 9, so that the center boss 11 is formed into a predetermined length in an axis direction. Three airway tubes 18 extending in the axis direction are formed in the center boss 11 to communicate with the suction lumens 3a, 3b, and 3c.

Figure 1:
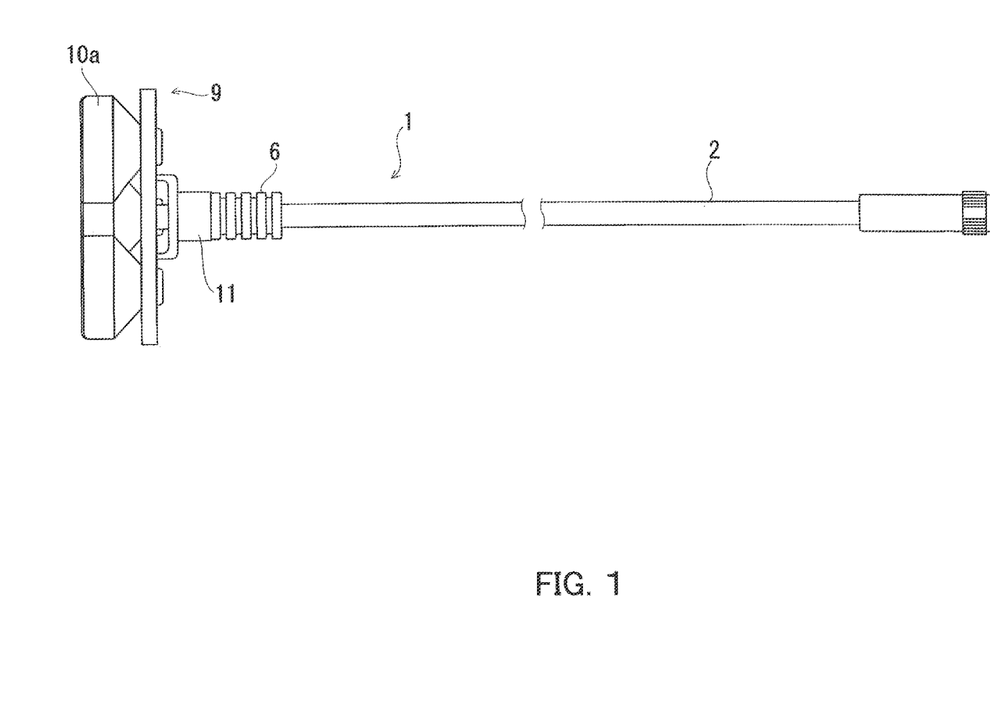
FIG. 1 is a partially-omitted front view of an organ sucking and grasping tool according to an embodiment of the present invention.
Figure 2:
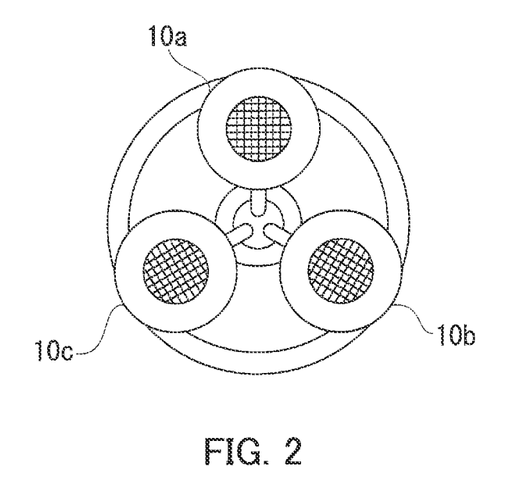
FIG. 2 is a left side view of FIG. 1.
Figure 3:
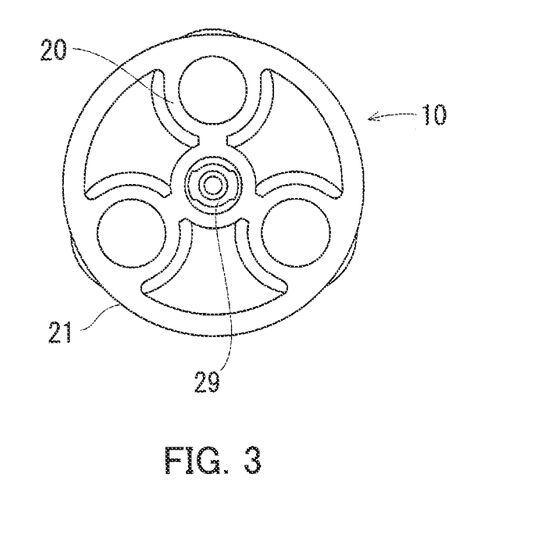
FIG. 3 is a right side view of FIG. 1.
Figure 4:
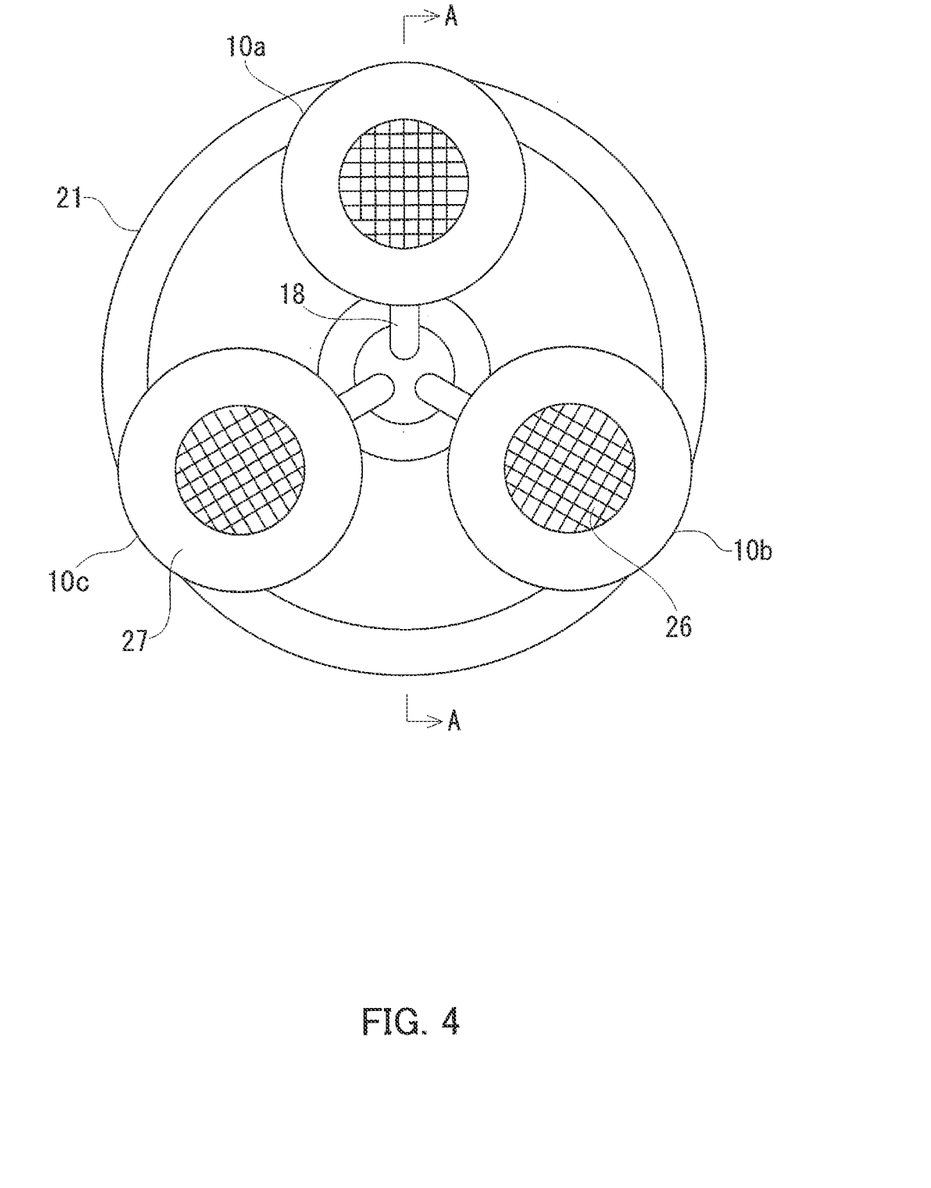
FIG. 4 is an enlarged view of FIG. 2.

The holder 9 includes the foregoing center boss 11, a plurality of suction cup attachments 20 jutting out in a radial direction from the boss, and a ring 21 fixed to tip portions of the attachments. The suction cup attachments 20 are provided with circular attachment holes 22. The attachment holes have a plurality of (here, three) suction cups 10a, 10b, and 10c attached thereto with end portions of the suction cups fitted by insertion to the attachment holes in such a manner that the suction cups are regularly spaced from each other in a circumferential direction in a side view (FIG. 2). Namely, the suction cups 10a, 10b, and 10c are arranged in such a manner that a line connecting the respective centers of the suction cups form a regular triangle. To retain the shape of the ring 21, a metallic wire 21a made of stainless steel is buried in the ring 21. Despite the presence of the metallic wire 21a, the ring 21 is given flexibility allowing the ring 21 to be bent to a certain degree.

The suction cup attachment 20 corresponds to the conventional dome-shaped member. However, the suction cup attachment 20 has a flat-plate shape, unlike the shape of the dome-shaped member. This suppresses the height (length in an axis direction) of the suction cup attachment 20. For this reason, even when the suction cup attachment 20 is inserted into a chest cavity, the suction cup attachment 20 does not cause hindrance to usage thereof during handling, treatment, etc.

Each of the suction cups 10a, 10b, and 10c has an inner cavity expanded more widely as viewed from the attached end portion toward an open end portion thereof. The inner cavity has an inner surface provided with a plurality of small projections 23 for increasing suction force. In this example, the small projections 23 having laterally-long round shapes are provided at an equal distance in a circumferential direction. A suction hole 25 is formed at a side near the bottom of a funnel shape. One end of each of the airway tubes 18 is communicably connected to each suction hole 25. The other end of the airway tube 18 is connected to a corresponding one of the suction lumens 3a, 3b, and 3c at the center boss 11, as described above. The small projections 23 have the function of preventing blockage of the suction hole 25 with a body tissue sucked on these small projections, in addition to the function of increasing suction force described above. The presence of the small projections 23 makes it possible to prevent reduction in a suction area to encourage increase in suction force at each of the suction cups 10a, 10b, and 10c. The front side of the inner cavity functions as a suction port.

A mesh 26 made of polyester fiber, for example, is affixed to the inner cavity between the suction hole 25 and the small projections 23. The provision of the mesh 26 to partition the inner cavity is intended to allow entry even of a soft organ into a position near the suction hole 25 and to prevent blockage of the suction hole 25.

The open end of each of the suction cups 10a, 10b, and 10c is provided with a flange 27 of a flat-plate shape inwardly bent at a substantially right angle from an end edge. The provision of the flange 27 is intended to prevent a clearance to be caused if the suction cups 10a, 10b, and 10c fail to follow the deformation of an organ, as will be described later.

Each of the suction cups 10a, 10b, and 10c has an outer diameter of about 2 cm, and becomes functional to suck, grasp, move, and fix an organ in response to application of a negative pressure from 20 to 50 cmHg from a suction device as a suction source not shown in the drawings. The center axes of the suction cups 10a, 10b, and 10c, and the center axis of the center boss 11 of the holder 9 are both parallel to the center axis of the tube body 2.

A one-lumen type short tube 28 is connected to a rear end portion of the tube body 2 with a suction lumen of the tube 28 communicably connected to the suction lumens 3a, 3b, and 3c (FIG. 5). In preparation for use, a joint connector 29 connected to the foregoing suction device and a guidance rod (not shown in the drawings) are connected to the tube 28. FIG. 5 shows only a part relating to the suction cup 10a, and parts relating to the suction cups 10b and 10c are omitted.

Each of the suction cups 10a, 10b, and 10c and the holder 9 such as the suction cup attachment 20 are preferably made of transparent or semi-transparent materials for improving the performance of viewing through an endoscope.

A using method will be described next by referring to FIGS. 7 to 10. Regarding signs given to respective parts indicated by alphabetical characters in each drawing, A and B each show a trocar retained in a small incisional wound, C shows an abdominal wall, D shows a lung as an example of an organ, E shows an endoscope, F shows a small incision, G shows an electrical knife, and H shows forceps.

Figure 7:
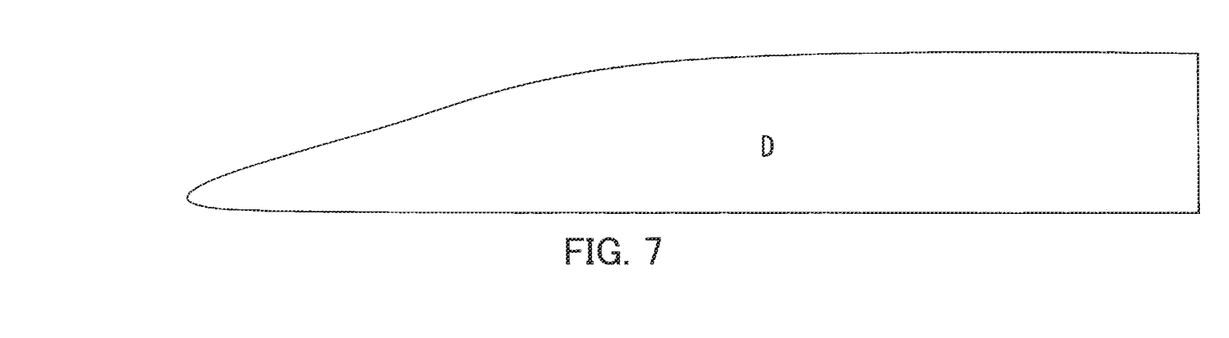
FIG. 7 is a working explanatory view for explaining exemplary use of the organ sucking and grasping tool.
Figure 8:
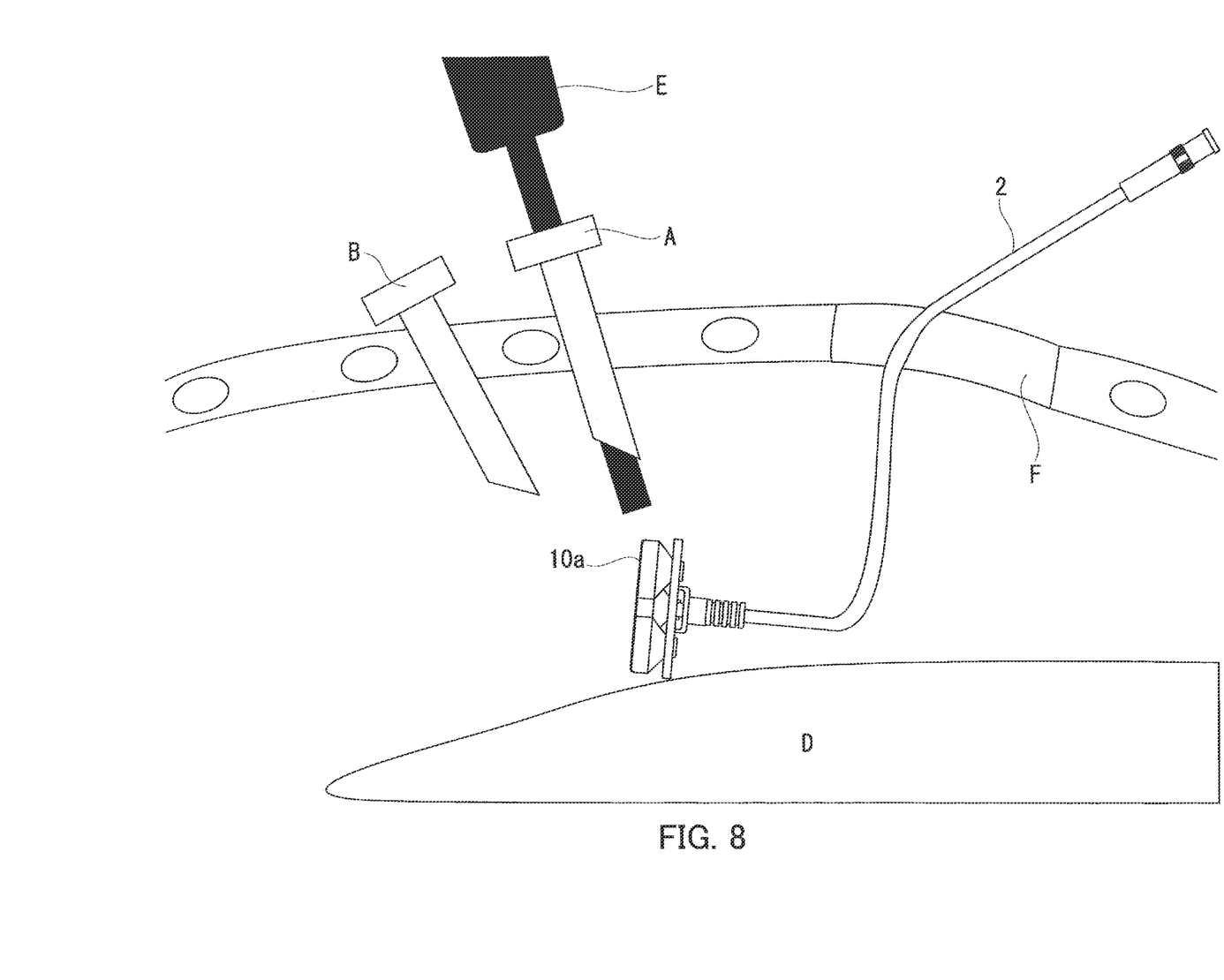
FIG. 8 is a working explanatory view for explaining the exemplary use.

In preparation for use, as shown in FIGS. 7 to 8, the trocars A and B are first stuck into the abdominal wall C, inserted toward the lung D in a body cavity, and retained therein. Then, the endoscope E is inserted into one trocar A, and the sucking and grasping tool 1 is inserted through the small incision F formed into a size from about 40 to about 50 mm at the abdominal wall C until the inserted tube body 2 reaches its substantially middle position. Regarding this insertion, as the small incision F is about 40 to about 50 mm and the ring 21 of the holder 9 is about 50 mm, it is expected that the outer edge of the ring 21 as it is will get caught on the small incision F at the abdominal wall C to become hindrance to the insertion. As the ring 21 is made of silicone rubber or soft resin and reducible in diameter together with the suction cups 10a, 10b, and 10c, the insertion is achieved easily.

Figure 9:
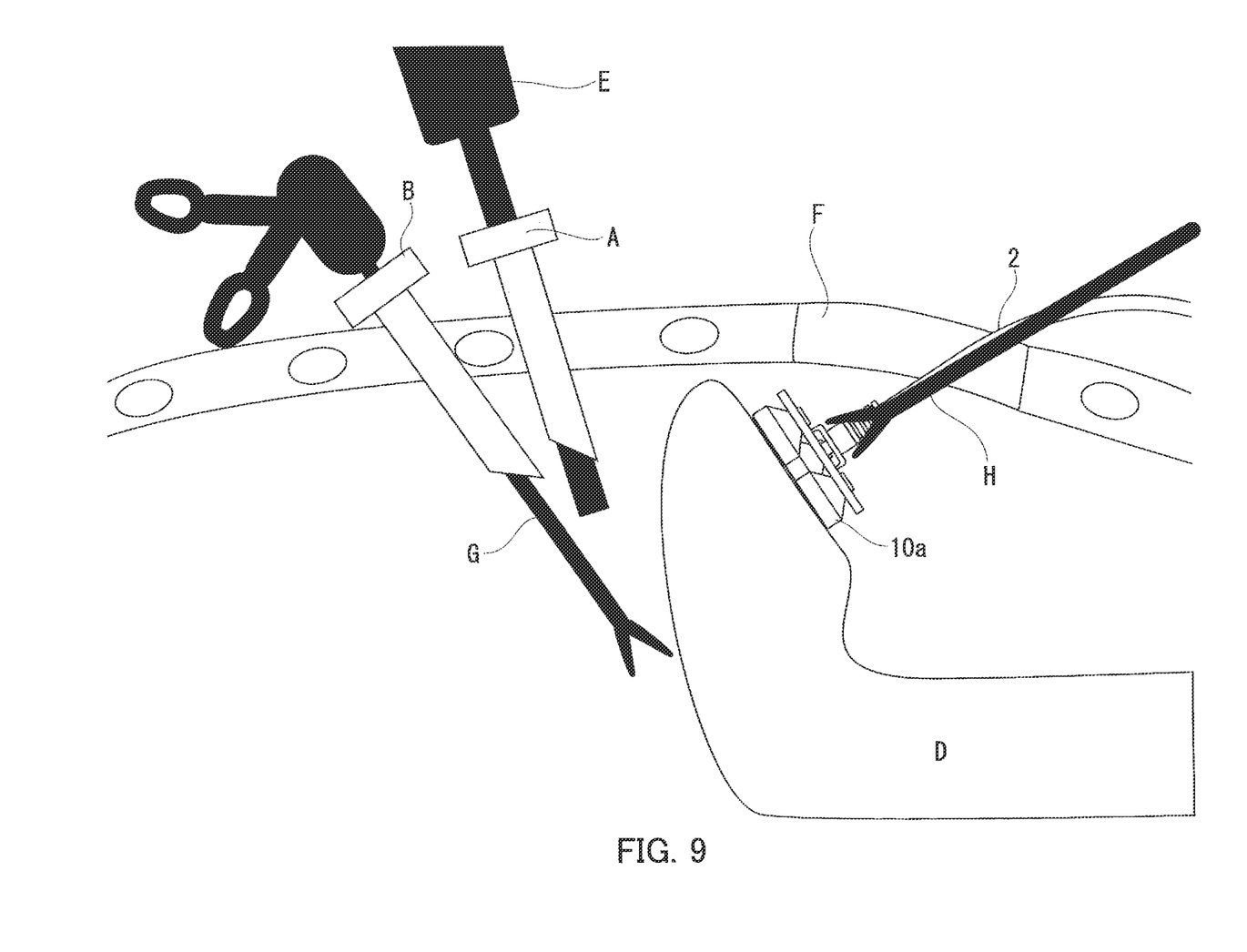
FIG. 9 is a working explanatory view for explaining the exemplary use.

The sucking and grasping tool 1 is inserted further to guide the suction cups 10a, 10b, and 10c to positions closer to the lung D at which the lung D can be sucked easily, as shown in FIG. 8. Then, the suction device not shown in the drawings connected to the joint connector 29 is actuated separately to apply a negative pressure. As a result, as shown in FIG. 9, the soft surface of the lung D is sucked into the suction cups 10a, 10b, and 10c. In this sucking and grasping state, the suction hole 25 is not blocked by the small projections 23 or the mesh 26 to maintain a favorable sucking state. With the sucked state created by the suction cups 10a, 10b, and 10c, the sucking and grasping tool 1 is controlled in a degree of its insertion by being pulled back to the outside while being held in such a manner as to catch the outer peripheral surface of the coating tube 6 between the forceps H, thereby bringing an affected part of the lung D that may be the back side thereof, for example, to a position observable through the endoscope E. Then, under observation through this endoscope, the affected part is subjected to an operation such as resection with the electrical knife G inserted from the other trocar B.

Figure 10A:
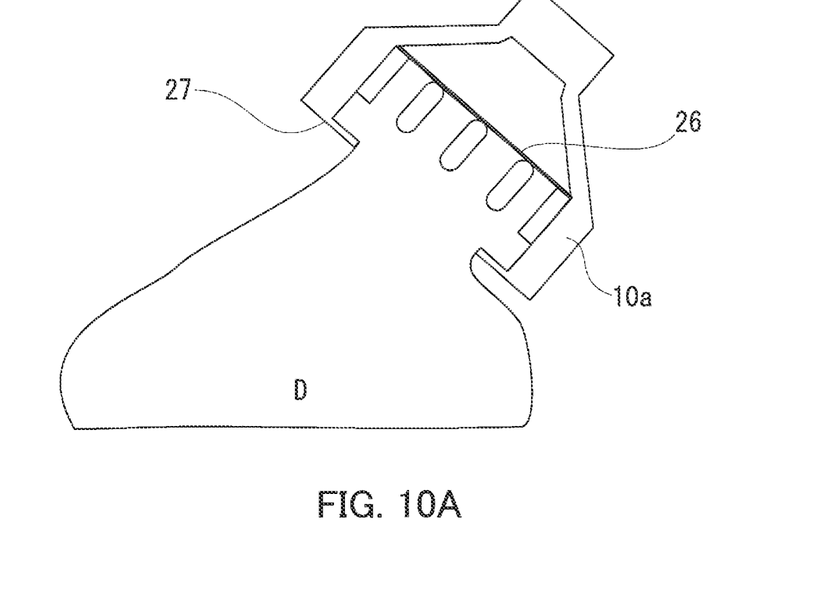
FIGS. 10A and 10B are a view for explaining how a flange works, and include FIG. 10A corresponding to the embodiment and FIG. 10B in the absence of a flange.

When the suction cups 10a, 10b, and 10c suck the soft surface of the lung D, the flange 27 suppresses the deformation of the lung D being sucked. Thus, as shown in FIG. 10A, the lung D is sucked into the suction cup 10a in a neat and stable posture without causing a clearance near the suction port, and is then subjected to an operation such as resection. This generates a state in which the lung tissue sucked in the suction cup is contracted in the inner cavity, so that the deformation of the lung can be suppressed during the inversion of the lung. This makes the suction cup less detachable from the lung D, making it possible to prevent slipping off of the suction cup.

Figure 10B:
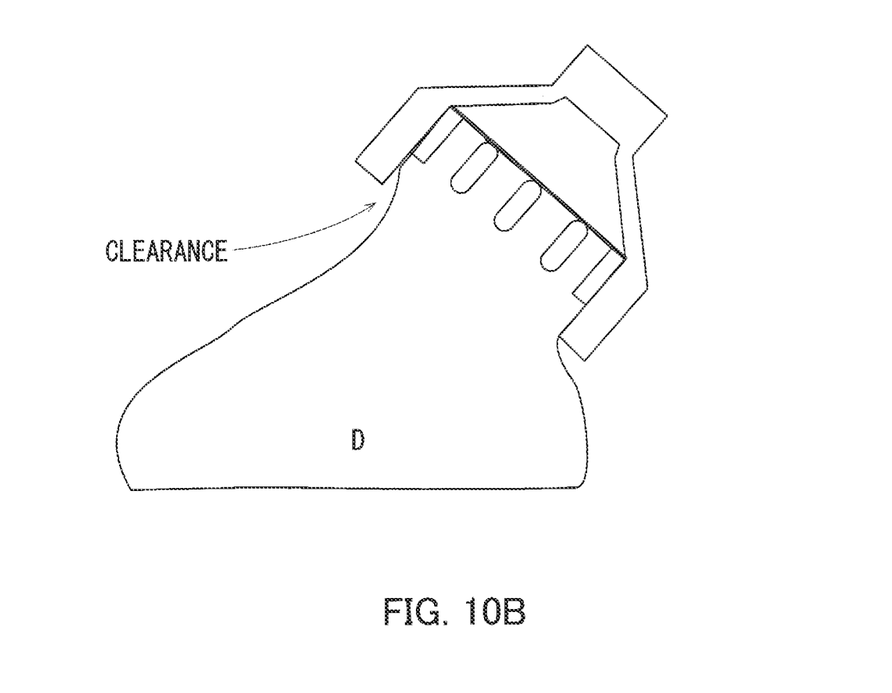

By contrast, as shown in FIG. 10B, sucking the lung D using a suction cup without the flange 27 disables the suction cup 10a to follow the deformation of the lung D. This inadvertently causes a clearance near the suction port, making it difficult to create the suction in a stable posture and making the suction cup easily detachable. Namely, the presence or absence of the flange 27 generates a clear difference in suction using the suction cup. A traction test was conducted on the foregoing issue using prototypes. As a result, each of the suction cups 10a, 10b, and 10c with the flange 27 shown in FIG. 10A is found to achieve significantly increased traction force even during traction in a horizontal direction.

After the operation, the motion of the foregoing suction device is stopped to stop the sucking and grasping of the surface of the lung D using the suction cups 10a, 10b, and 10c, thereby bringing the lung D to its original position where the affected part returns to the back side. Further, the sucking and grasping tool 1 is pulled out of the small incision F. During this pulling, if the holder 9 is a planar rigid member, the holder 9 gets caught on the small incision F at the abdominal wall C so cannot be pulled out easily. In this regard, as the holder 9 is made of relatively soft ring-shaped resin as described above, the holder 9 is reduced in diameter together with the suction cups 10a, 10b, and 10c and thus can be pulled out easily under reduced resistance. The sucking and grasping tool 1 can also be used for exclusion (depression) of an organ. The ring shape without a corner of the holder 9 makes it possible to prevent damage on a body tissue during the exclusion.

As described above, using the sucking and grasping tool 1 makes the ring-shaped holder 9 reducible in diameter, thereby allowing insertion into the small incision F and pulling out through the small incision F to be done smoothly and easily without hindrance. Further, as no reduction occurs in suction force generated by the suction cups 10a, 10b, and 10c, slipping off of the suction cups 10a, 10b, and 10c is prevented to allow elevation and exclusion of an organ reliably, even if the organ is soft and easily deformable. Additionally, as the ring shape without a corner of the holder 9 prevents damage on a body tissue during exclusion.

According to the present embodiment, changing the conventional dome-shaped member to the ring-shaped holder 9 described above allows reduction in the height of the sucking and grasping unit. This improves usage during handling, treatment, etc., and allows reservation of a viewing field for an endoscope and reservation of space for operations. Additionally, the presence of the metallic wire buried in the ring 21 of the holder 9 allows retention of the shape of the ring. Further, the provision of the disk-like flange 27 at the end edge of the suction cup makes it possible to prevent the occurrence of a clearance from the suction cup. As a result, the suction and fixation can be maintained stably. The traction test described above conducted on the corresponding prototype shows that traction force during traction is increased significantly even in the horizontal direction, a tissue sucked into the suction cup is contracted in the disk-shape part to allow suppression of the deformation of the lung during the inversion of the lung. In addition, the suction cup becomes less detachable to prevent slipping off of the suction cup.

The ring-shaped holder 9 in the embodiment is merely described as a preferred example and does not exclude other modifications. The other members are also described merely as examples and may have shapes or configurations different from those illustrated in the drawings. The present invention can certainly be changed or modified freely in terms of detailed design, etc., within a range described in CLAIMS.

The invention claimed is:

1. An organ sucking and grasping tool comprising:
    a suction tube body having a front end portion;
    a plurality of suction cups for organ suction, each of the suction cups having an open end portion and being provided at a front end portion of the suction tube body, the organ sucking and grasping tool being configured to sucking, elevate and grasp a soft surface of an organ over a specific area using suction force generated by the plurality of suction cups;
    a ring-shaped holder made of silicone rubber or soft resin is provided at the front end portion of the suction tube body, the holder comprising:
        a center boss;
        a plurality of suction cup attachments jutting out in a radial direction from the center boss; and
        a ring fixed in such a manner as to connect respective tip portions of the suction cup attachments, wherein a metallic wire is buried in the ring;
    wherein each of the suction cup attachments includes at least one attachment hole, and an end portion of each suction cup opposite the open end portion is secured in said attachment hole to hold the suction cup in place; and
    wherein an annular flange is inwardly bent from an edge of the open end portion of each suction cup, the annular flange being configured to follow a deformation of the surface of the organ and to suppress the deformation of the organ.

2. The organ sucking and grasping tool according to claim 1, wherein
    the front end portion of the suction tube body is covered with a protective pipe and is connected to the center boss of the holder.

3. The organ sucking and grasping tool according to claim 2, wherein
    a coating tube is fitted to the protective pipe and has an outer peripheral surface provided with an undulated part.

4. The organ sucking and grasping tool according to claim 1, wherein
    the suction cups include three suction cups arranged at the holder in such a manner that a line connecting the respective centers of the suction cups form a regular triangle.

5. The organ sucking and grasping tool according to claim 1, wherein
    the suction cups have center axes parallel to the center axis of the tube body.

* * * * *